United States Patent [19]

Childers et al.

[11] Patent Number: 5,527,508

[45] Date of Patent: * Jun. 18, 1996

[54] METHOD OF ENHANCED PENETRATION OF LOW VAPOR PRESSURE CHEMICAL VAPOR STERILANTS DURING STERILIZATION

[75] Inventors: Robert W. Childers, Garner; Donald R. Gagne, Raleigh, both of N.C.

[73] Assignee: American Sterilizer Company, Erie, Pa.

[*] Notice: The portion of the term of this patent subsequent to Jul. 25, 2014, has been disclaimed.

[21] Appl. No.: 973,372

[22] Filed: Nov. 12, 1992

[51] Int. Cl.$^6$ ........................................ A61L 2/20
[52] U.S. Cl. ............................... 422/33; 422/28
[58] Field of Search ................... 422/28, 33, 39, 422/292, 295

[56] References Cited

U.S. PATENT DOCUMENTS

| | | |
|---|---|---|
| 4,296,067 | 10/1981 | Nasman et al. . |
| 4,348,357 | 9/1982 | Bithell . |
| 4,372,916 | 2/1983 | Chamberlain et al. . |
| 4,380,530 | 4/1983 | Kaye . |
| 4,642,165 | 2/1987 | Bier ............................................ 203/12 |
| 4,687,635 | 8/1987 | Kaehler et al. ......................... 422/33 X |
| 4,744,951 | 5/1988 | Cummings et al. . |
| 4,764,351 | 8/1988 | Hennebert et al. .................... 422/33 X |
| 4,909,999 | 3/1990 | Cummings et al. ................. 422/292 X |
| 4,956,145 | 9/1990 | Cummings et al. ...................... 422/28 |
| 5,008,079 | 4/1991 | Wutzler et al. ..................... 422/295 X |

FOREIGN PATENT DOCUMENTS

| | | |
|---|---|---|
| 0302419 | 2/1989 | European Pat. Off. . |
| 0302420 | 2/1989 | European Pat. Off. . |
| WO9317726 | 9/1993 | WIPO . |

OTHER PUBLICATIONS

Young et al, "Temperature Profiles and Sterilization Within a Dead-Ended Tube," Journal of Parental Science & Technology Jul.–Aug. 1992.

Perkins, Principles and Methods of Sterilization in Health Sciences, 2nd Ed.

Primary Examiner—Robert J. Warden
Assistant Examiner—E. Leigh Dawson
Attorney, Agent, or Firm—Jones, Day, Reavis & Pogue

[57] ABSTRACT

A method of improving the delivery of low vapor pressure chemical vapor sterilant into complex objects, such as lumens and piping dead legs using vapor compression.

12 Claims, 1 Drawing Sheet

METHOD OF ENHANCED PENETRATION OF LOW VAPOR PRESSURE CHEMICAL VAPOR STERILANTS DURING STERILIZATION

FIELD OF INVENTION

The present invention relates to sterilization of various articles and, in particular, to the use of vapor compression of low vapor pressure chemical vapor sterilants to sterilize articles of complex and irregular shape.

BACKGROUND OF THE INVENTION

Complex objects which may contain a variety of narrow apertures, holes or tubes are difficult to sterilize. In particular, open ended lumens, internal cavities, deadlegs and flat surfaces in close proximity present difficulties. In situ sterilization of freeze dryers and sterilization of deadlegs and lumens created by piping external to the freeze drying chamber that is corroded, has a small external leak, or an extremely high depth to diameter ratio can also present an extreme challenge. Moreover, lumens and deadlegs which absorb sterilant material to any degree can also be difficult to sterilize.

Sterilization of complex objects is currently accomplished by using wet or dry heat, chemicals, ionizing radiation, electron beams, microwaves, arc discharges, lasers, plasmas and high vapor pressure chemical gases. Heat, penetrating radiation, or high vapor pressure chemical gases, have been preferred for sterilizing articles of irregular shape because of their ability to effectuate sterilization within narrow apertures, holes and tubes which are otherwise difficult to access. Each of these methods, however, has limitations and problems.

For the purposes of this invention the term sterilization means a 6 log (or greater) reduction in bioburden.

A number of these sterilization methods are discussed in "Principles and Methods of Sterilization in Health Sciences", second edition, written by John J. Perkins and published by Charles C. Thomas of Springfield, Ill.

A table for dry heat sterilization containing adequate exposure times for a variety of temperatures contained in Perkins on page 289 is reproduced as Table A below.

TABLE A

Dry Heat Sterilization Time-Temperature Ratios

| Exposure Temperature | | |
|---|---|---|
| Degrees C. | Degree F. | Exposure Time |
| 180 | 356 | 30 minutes |
| 170 | 340 | 1 hour |
| 160 | 320 | 2 hours |
| 150 | 300 | 2½ hours |
| 140 | 285 | 3 hours |
| 121 | 250 | 6 hours |

Dry heat sterilization does not require any pressure, but it is very difficult, and quite impractical, to heat complicated objects such as an entire freeze dryer and its associated piping to these high temperatures using electric or gas heaters or with hot air.

Moist heat sterilization is much easier to implement since the introduction of saturated steam into a complicated object such as a freeze dryer will supply both the heat and the moisture. A table for moist heat sterilization containing adequate exposure times for a variety of temperatures (Perkins, page 161) is reproduced as Table B, below.

TABLE B

Moist Heat Sterilization Time-Temperature Ratios

| Exposure Temperature | | Corresponding | |
|---|---|---|---|
| Degrees C. | Degree F. | Pressure | Exposure Time |
| 138 | 280 | 49.2 psia | 0.8 Minutes |
| 132 | 270 | 41.9 psia | 2 Minutes |
| 125 | 257 | 33.7 psia | 8 Minutes |
| 121 | 250 | 29.8 psia | 12 Minutes |
| 118 | 245 | 27.3 psia | 18 Minutes |
| 116 | 240 | 25.0 psia | 30 Minutes |

Both Tables A and B contain exposure times and do not account for the time required for all of the components within the object such as a freeze dryer and its associated piping to come up to temperature.

According to "Temperature Profiles and Sterilization within a Dead-ended Tube", written by Jack J. Young and Barbara L. Ferko and published in the July-August issue of the Journal of Parenteral Science & Technology, the time for a dead leg to come up to temperature can be considerable.

The data from Table III in Young et al for dead leg sterilization at 121° C. is reproduced in Table C, below. Note that all of these times, which account for coming up to temperature, are much longer than the exposure times recommended by Perkins (Table B). Freeze drying piping dead legs are typically sloped at around 5° so they will drain, and they often are longer than those discussed in Young, et al. Thus, it would be expected to require sterilization times in excess of 358 minutes to completely sterilize a freeze dryer and its associated piping.

TABLE C

Estimated Sterilization Times Within Dead-ended Tubes For Varying Tube Orientations

| Distance up Tube | Percent into Tube | Sterilization Time (minutes) | | |
|---|---|---|---|---|
| | | Vertical up | 45° Up | 5° Up |
| 1.8 cm | 19.2 | 29.8 | 24.0 | 23.5 |
| 3.1 cm | 33.0 | 31.2 | 54.3 | 72.5 |
| 4.3 cm | 45.8 | 64.4 | 117.3 | 206.0 |
| 5.6 cm | 59.8 | 68.0 | 121.4 | 358.3 |
| 6.9 cm | 73.6 | 101.3 | N.T. | N.T. |
| 8.1 cm | 86.4 | 167.3 | N.T. | N.T. |

The time required to heat up, sterilize, and cool down a massive object such as a freeze dryer will substantially reduce the time available for the Object (freeze dryer) to be used for its intended purpose (freeze drying). The addition of "jackets" to heat and cool the chamber and condenser on a freeze dryer can decrease this time substantially, i.e. from 24 hours to 8 hours, but at the expense of thermally stressing the chamber, condenser and associated piping. This thermal stress, when alternated with the extreme cold (−40° C.) associated with freeze drying will propagate leaks and can actually cause the chamber and/or condenser to crack and have to be replaced periodically at great expense in time.

Gaseous chemical sterilization agents such as ethylene oxide can sterilize within 2½ hours, but an extended aeration time, up to 24 hours, is required to remove the residuals. Disposal of the expended sterilant is also difficult because it is considered both toxic and carcinogenic. Some states, California for example, require that any products that have been in contact with ethylene oxide been in contact with ethylene oxide be labeled as being processed with a known carcinogen. This would put a manufacturer at a disadvantage with a competitor who used a different sterilization process.

Use of pure concentrated ethylene oxide sterilant can be dangerous because it is explosive when mixed with oxygen (both during and at the end of the cycle when air is admitted into the chamber) so it is typically mixed with a diluent such as Freon (which is being banned because it is an ozone depleter) before it is introduced into the sterilization chamber.

Ionizing radiation must be of sufficiently high energy to penetrate articles effectively. This necessitates the use of x-rays and/or gamma rays, both of which require large and expensive apparatus and are generally hazardous. Furthermore, ionizing radiation could not be expected to penetrate effectively around through and into all of the metal components and down the piping within a complex object such as a freeze dryer.

Use of low vapor pressure chemical vapor sterilants avoid some of the above-mentioned concern and limitations, but because it is also difficult for them to penetrate into the holes, openings and apertures of complex shaped articles, several methods attempting to enhance their penetration characteristics have been considered. These methods typically include: (1) deep evacuation of the sterilizing chamber prior to introduction of the sterilant; (2) alternating of evacuation pulses and sterilant introduction pulses; (3) increasing sterilant concentration and/or pre-injection chamber pressure; (4) direct coupling and flowing or recirculating the sterilant through the lumen or object; and (5) continuously "pressure pulsing" during the sterilization phase.

U.S. Pat. No. 4,348,357 provides a method for plasma pulsations. U.S. Pat. No. 4,296,067 provides a method of sterilizing material, especially bandage and surgical instruments, in a steam autoclave operating as near to vacuum as possible. And finally, U.S. Pat. No. 4,372,916 discloses a method which utilizes alternating evacuation and sterilant introduction pulses.

Each of the above mentioned methods are designed to enhance sterilant penetration, but all continue to fall short of being ideal.

Achieving an increase in sterilant penetration performance by use of a deep vacuum as suggested by U.S. Pat. No. 4,296,067 has been verified. Tests ran by AMSCO, and contained in Table D, below verified that this method would work for hydrogen peroxide vapor. However, as seen in the table this concept when used with low vapor pressure gases requires the vacuum level to be of the order of 1 Torr or less to achieve best results. This requirement results in excessive pump down times, and expensive pumping equipment. In addition the results obtained using this technique are achievable with fewer deep vacuum pulses when using the invention proposed herein.

TABLE D

| Average Hydrogen Peroxide Vapor Sterilant Penetration into 1 cm ID × 120 cm Deep Passivated Stainless Steel Deadlegs | | | | |
|---|---|---|---|---|
| Pre-Injection | 2½ Ft³ Chamber Depth of Penetration | | 154 Ft³ Chamber Depth of Penetration | |
| Vacuum Level | (cm) | (percent) | (cm) | (percent) |
| 10 Torr | N.T. | N.T. | 60 | 50 |

TABLE D-continued

| Average Hydrogen Peroxide Vapor Sterilant Penetration into 1 cm ID × 120 cm Deep Passivated Stainless Steel Deadlegs | | | | |
|---|---|---|---|---|
| Pre-Injection | 2½ Ft³ Chamber Depth of Penetration | | 154 Ft³ Chamber Depth of Penetration | |
| Vacuum Level | (cm) | (percent) | (cm) | (percent) |
| 5 Torr | 80 | 67 | 60 | 50 |
| 2 Torr | 80 | 67 | 73 | 61 |
| 1 Torr | 90 | 75 | 87 | 73 |
| 0.1 Torr | 115 | 96 | N.A. | N.A. |

Sterilant penetration results were not available for the large chamber because the vacuum system was unable to evacuate to 0.1 Torr. A very expensive pump would have been capable of doing so but the cycle time would have increased substantially in the process.

A dead leg shape containing coupons inoculated with 1×10⁶ Bacillus Steorothemophilus spores as illustrated in Figure L was placed inside an 81 liter chamber that had a leak rate (pressure rise) of 150 microns per minute. The chamber was then evacuated to 0.1 Torr prior to the introduction of hydrogen peroxide vapor which increased the pressure to about 6 Torr. After a six minute sterilize hold the chamber was re-evacuated and the sterilize pulse repeated. After 9 sterilize pulses all the coupons were sterile.

This same dead leg was located external to, but attached to the chamber using the KF40 adapter. The chamber leak rate (pressure rise) now increased to 230 microns per minute due to a leak rate into the dead leg of about 0.0085 standard liters per minute. After a 9 pulse sterilize cycle, which was identical to that ran when the dead leg was inside the chamber, none of the coupons was found to be sterile. The enhanced penetration due to the use of a deep pre-injection vacuum was insufficient to overcome the small leak in the external dead leg.

Thus, when sterilizing large, complex objects such as a freeze dryer the deep pre-injection vacuum was found to be very expensive to implement, to have long cycle times and to be unable to sterilize external piping dead legs with small leaks.

The method of alternating evacuation pulses and sterilant introduction pulses discussed in U.S. Pat. No. 4,372,916 was evaluated on the 154 Ft³ chamber using hydrogen peroxide vapor. The results of this evaluation for an evacuation of 1 Torr are included in Table E. The test was conducted using 1cm I.D.×120 cm deep passivated stainless steel dead legs containing inoculated with 1.0×10⁶ Bacillus steorothemophilus spores as the biological challenge.

TABLE E

| Depth of Penetration from open end (cm) | Number Positive/Number Tested for Sterility | | | |
|---|---|---|---|---|
| | 4 Sterilize Pulses | 8 Sterilize Pulses | 16 Sterilize Pulses | 32 Sterilize Pulses |
| 0 | 0/6 | 0/2 | 0/2 | 0/2 |
| 10 | 0/6 | 0/2 | 0/2 | 0/2 |
| 20 | 0/6 | 0/2 | 0/2 | 0/2 |
| 30 | 0/6 | 0/2 | 0/2 | 0/2 |
| 40 | 0/6 | 0/2 | 0/2 | 0/2 |
| 50 | 0/6 | 0/2 | 0/2 | 0/2 |
| 60 | 0/6 | 0/2 | 0/2 | 0/2 |
| 65 | 0/6 | 0/2 | 0/2 | 0/2 |

TABLE E-continued

| Depth of Penetration from open end (cm) | Number Positive/Number Tested for Sterility | | | |
|---|---|---|---|---|
| | 4 Sterilize Pulses | 8 Sterilize Pulses | 16 Sterilize Pulses | 32 Sterilize Pulses |
| 70 | 0/6 | 0/2 | 0/2 | 0/2 |
| 75 | 3/6 | 0/2 | 0/2 | 0/2 |
| 80 | 3/6 | 0/2 | 0/2 | 0/2 |
| 90 | 4/6 | 1/2 | 0/2 | 0/2 |
| 100 | 6/6 | 2/2 | 1/2 | 0/2 |
| 110 | 6/6 | 2/2 | 1/2 | 0/2 |
| 120 | 6/6 | 2/2 | 2/2 | 0/2 |

This method would work but it was found to take 16 to 32 sterilize pulses to be equal in performance to the deep pre-injection vacuum method discussed previously.

Simply increasing the concentration of the hydrogen peroxide vapor in the 154 cubic foot chamber was also tested at various pre-injection vacuum levels. Table F contains the data for this method.

TABLE F

Average Hydrogen Peroxide Vapor Sterilant Penetration into
1 cm I.D. × 120 cm Deep Passivated Stainless Steel Deadlegs

| Pre-Injection Vacuum Level | Amount of Sterilant Injected per pulse | Depth of Penetration | |
|---|---|---|---|
| | | (cm) | (percent) |
| 10 Torr | 28 grams | 58 | 48 |
| | 35 grams | 60 | 50 |
| | 42 grams | 75 | 63 |
| | 56 grams | 90 | 75 |
| 5 Torr | 35 grams | 60 | 50 |
| 2 Torr | 28 grams | 60 | 50 |
| | 35 grams | 73 | 61 |
| | 42 grams | 80 | 67 |
| | 56 grams | 76 | 63 |
| 1 Torr | 56 grams | 87 | 73 |

The data for a 4 pulse sterilization cycle shows that increasing the concentration will enhance penetration somewhat but will not result in the desired level of penetration performance. Residual levels were higher after aeration when increased amounts of sterilant were introduced. This is presumably because the saturation, or dew point, conditions were exceeded and condensation occurred. Further increase in the amount injected resulted in excessive condensation and prolonged aeration as well as decreased depth of penetration.

The direct coupling process described in U.S. Pat. No. 4,372,916 is not always practical because all dead ended configurations must be converted to flow through configurations in order to implement such a method. This restructuring would be particularly impractical for objects contained in, for example, a freeze dryer chamber and condenser.

There is a need for a method which can sterilize complex objects by using low vapor pressure chemical vapor sterilants. There is a further need for enhancing the penetration of such sterilants into the openings and apertures of such complex objects being sterilized. There is a further need for a method which can be used in both small scale applications and large scale applications without being prohibitive with respect to cost of sterilization cycle time.

SUMMARY OF INVENTION

It is therefore a main object of the present invention to provide a method of enhancing the penetration of low vapor pressure chemical vapor sterilants into the apertures and openings of complex objects.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

To achieve these objects and in accordance with the purpose of the invention, the present invention provides a method of enhancing the vapor sterilant penetration of complex objects such as lumens by using air dry air (less than 5% R.H.) or inert gas to drive the vapor that has diffused into closed or open ended lumens by further down the lumen than it could naturally diffuse. The addition of the air, or dry air or inert gas creates a higher pressure differential, and thus flows, than would naturally occur by pulsing in a low pressure sterilant. This more rapid flow helps to overcome absorption and decomposition of the sterilant. For purpose described here in low vapor sterilant means any gas sterilant where the active component has a partial pressure less than 30 mm of Hg. A vacuum is pulled following the vapor compression, removing the residual sterilant vapors (and humidity) and thus preparing the system for the next sterilization pulse.

The method may also be combined with other known methods such as deep evacuation of the chamber prior to the introduction of the sterilant, alternating of evacuation pulses and sterilant introduction pulses, increasing sterilant concentration, and direct coupling and flowing the sterilant through the article.

DETAILED DESCRIPTION OF THE PREFERRED EMBODIMENT

The present invention overcomes the disadvantages of current sterilization methods by using air, dry air, sterilant laden air or an inert gas such as helium or nitrogen to compress the vapor sterilant that has diffused into closed and opened end lumens. The air acts as a piston which pushes and compresses the vapor further of the lumen and is sufficiently fast so that diffusion, decomposition or an external leak does not offset the enhancing effect of the compression. The concentrated sterilant gases or vapors then sterilize the most remote portion of the lumen in a timely and efficient manner. Opened end lumens will behave similarly to closed end lumens with vapor entering from each end. The sterilant will be pushed toward the center of the lumen when subjected to vapor compression. Typically the vapor compression itself has a duration of less than one minute but longer air bleed times are also helpful. After an exposure time, a vacuum pulldown follows the vapor compression in order to remove the residual sterilant vapors and eliminate humidity in preparation for the next sterilization pulse. This is an advantage for sterilants whose allowable concentrations are maximized when the pre-introduction humidity is at a minimum.

In a first embodiment of the invention, a closed end lumen is placed in a closed sterilization chamber at atmospheric pressure (760 Torr). The chamber is first evacuated to a pressure of less than or equal to 40 Torr, preferably between about 0.1 Torr to 10 Torr. Sterilant vapors are then introduced, raising the pressure in the chamber to a pressure which is greater than or equal to twice the initial, evacuated pressure, typically between 0.2 Torr and 80 Torr, preferably between about 6 Torr and 60 Torr. The preferred sterilant vapors are generated from electronic grade hydrogen peroxide, food grade hydrogen peroxide, peracetic acid, acetic acid, or mixtures thereof. The vapor is allowed to distribute itself throughout the chamber and into the dead end lumen for a time period which is normally less than or equal to twice the half life of the sterilant, based upon the environment within the chamber. For purpose here the half life is that time required for the sterilant concentration to be reduced by ½ either due to decomposition or absorption.

The vapor compression pulse begins when air, dry air, sterilant laden air, or some other inert gas such as helium or nitrogen, and mixtures thereof, is admitted into the chamber. Consequently, the pressure within the chamber is raised to a pressure typically greater than 6 times the previous pressure preferably between about 36 Torr and 360 Torr, within a pre-determined time T. Time T is typically less than 1 minute in duration. The sterilant is then allowed to remain inside the tube for a time period which is normally greater than or equal to its half life while inside the tube. The chamber is then evacuated again to a pressure of less than or equal to 40 Torr and the procedure is repeated until sterilization is achieved.

In a second embodiment of the invention, an opened end lumen is placed in a closed sterilization chamber at atmospheric pressure (760 Torr). Sterilant vapors are introduced from each end of the lumen. Similarly, vapor compression pulsations enter the opened end lumen from each end and the sterilant vapor is pushed further into the lumen than it would otherwise diffuse. The sterilization process is then carried on in essentially the same manner as that for a closed end lumen.

In determining the time T in which the pressure is raised to achieve vapor compression and the number of times the procedure must be repeated in order to achieve an optimum kill potential, the following calculations are considered.

For the sake of simplicity, it will be assumed that the half life of the sterilant inside the tube is equal to the time it takes for the concentration at the dead end of the tube to rise an amount equal to ¼ of the average concentration gradient between the inlet of the tube and the dead end of the tube. At time T=0, the concentration at the inlet is equal to C and the concentration at the dead end is 0. At time T=HL (half life of sterilant inside tube), the concentration at the inlet has fallen to ½ C and the concentration at the dead end has risen to ¼×((C+C/2)/2−0)=3/16 C. At time T=2HL, the concentration at the inlet has fallen to ¼ C and the concentration at the dead end has become ¼×((½ C+¼ C)/2+3/16 C)+½×3/16 C=3/32 C (since only half of what was present at the dead end of the tube at time T=HL remains at time T=2HL).

This pattern continues until, after an infinite sterilize hold period, the total kill potential (concentration×time) at the inlet of the tube can be calculated as the sum of the average kill potentials for each half life interval. This is found to be equal to an infinite series:

$$HL*(C+C/2)/2+HL*(C/2+C/4)/2+HL*(C/4+C/8)/2+HL*(C/8+C/16)/2+HL*(C/16+C/32)/2+ \ldots$$

which simplifies to $$(3*HL*C/2)*(½+¼+⅛+1/16 \ldots)$$

and finally to $$3*HL*C/2=\text{kill potential at inlet to tube}.$$

The kill potential at the dead end of the tube is found in a similar manner. However, the series is slightly more complex since the first time half life interval is different from the remaining half life intervals. After an infinite sterilize hold period, the total kill potential results in an infinite series:

$$HL*(0+3C/16)/2+HL*(3C/16+3C/32)/2+HL*(3C/32+3C/64)/2+HL*(3C/64+3C/128)/2+HL*(3C/128+3C/256)/2+ \ldots$$

which simplifies to $$HL*3C/32+HL*9C/32*(½+¼+⅛+1/16 + \ldots)$$

and finally to $$3*HL*C/8=\text{kill potential at the dead end of tube}.$$

Thus, it would be expected to require four times as many sterilize pulses to sterilize the dead end of the tube as it would to sterilize the inlet to the tube.

By using these formulas it can be determined that if a 6:1 vapor compression pulse were to occur from the inlet of the tube towards the end of the tube at time T=2HL, the entire vapor contents of the tube would be compressed into the bottom one sixth of the tube near the dead end. Hence, the vapor concentration at the dead end would then be ((C/4+3C/32)/2)*6=66C/64.

Furthermore, if the air used to compress the vapor was also sterilant laden, with concentration C no diffusion from the dead end of the tube would occur. The sterilant concentration at the dead end would then be reduced only by degradation according to the half life relationship.

In contrast, after a total sterilize time of T=4 HL, the kill potential at the inlet of the tube without vapor compression will be $$3HL*C/4+3HL*C/8+3HL*C/16+3HL*C/32=47HL*C/32.$$

In a similar manner, the kill potential at the dead end of the tube with vapor compression will be $$3H*C/32+9HL*C/32+3HL*C/4+3HL*C/8=3HL*C/2.$$

These two kill potentials are nearly identical meaning that the sterilization time at the dead end of the tube is nearly equal to the sterilization time at the inlet of the tube.

BRIEF DESCRIPTION OF THE DRAWINGS

The present invention can best be understood by reference to the drawings, in which.

DETAILED DESCRIPTION OF THE DRAWINGS

FIG. 1

Figure 1:
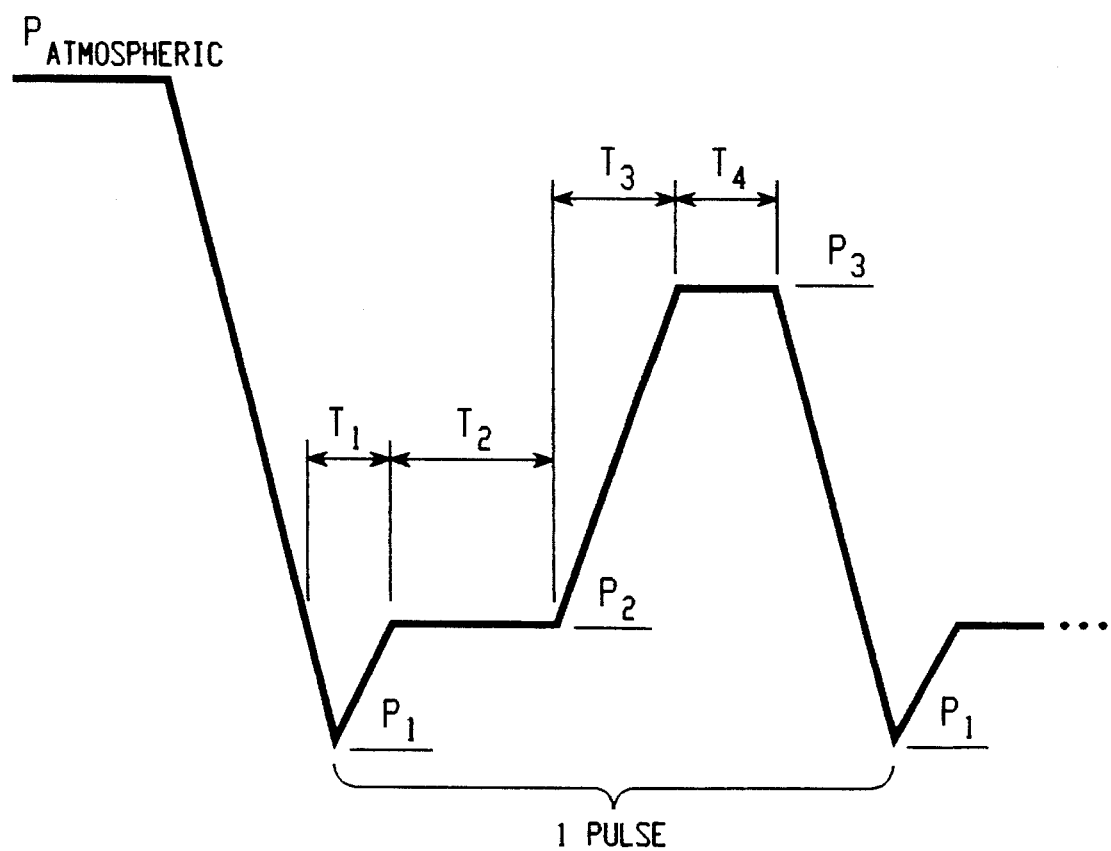
FIG. 1 is a schematic diagram illustrating the sterilization cycle of the present invention

The invention will be described in reference to FIG. 1, which illustrates a portion of a vapor compression sterilization cycle. Typically, the sterilization chamber is initially at atmospheric pressure (760 Torr).

As depicted in FIG. 1, the sterilization chamber is first evacuated to a pre-selected pressure $P_1$, typically less than or equal to 40 Torr. Sterilant vapors are then introduced raising the pressure in the chamber to a second pre-determined pressure, $P_2$ typically at least twice $P_1$ in a pre-determined Time $T_1$. $P_2$ is limited by the nature of the low pressure sterilant. The vapor is allowed to distribute itself throughout the chamber (including the dead end lumens) for a pre-determined time $T_2$, which is normally less than or equal to twice the half life of the sterilant based upon the environment within the chamber. The vapor compression begins by admitting the air, dry air sterilant laden air or inert gas ("Pressure Gas") into the chamber. The Pressure Gas is admitted into the chamber raising the pressure to a third pre-determined pressure, $P_3$, within a third pre-determined Time $T_3$. Time $T_3$ is typically less than 1 minute in duration. Pressure $P_3$ is typically greater than six times pressure $P_2$. The Pressure Gas and sterilant are then allowed to remain inside the tube for a fourth pre-determined time, $T_4$, which is normally greater than or equal to the half of the sterilant life while inside the tube. The chamber is then evacuated again to pressure $P_1$ and the procedure is repeated.

The pressure, time ranges and number of pulsations will vary between articles, depending on the particular object and its application. The following are but illustrative examples of the present invention as applied on various samples.

EXAMPLES

Example 1

Biologicals consisting of $10^6$ *Bacillus steorothemophilus* spores is placed along stainless steel strips of 120 cm, every 10 centimeters. The steel strips are slide down into a 1 cm ID×120 cm deep passivated stainless steel dead end tube. The tube is then placed inside a 2½ cubic foot chamber at atmospheric pressure. The chamber is first evacuated to various pressure ranging from 0.1 Torr to 5 Torr. Hydrogen peroxide vapors are then introduced, raising the pressure in the chamber by about 6 Torr. The hydrogen peroxide vapor is generated from a solution of 31% hydrogen peroxide by weight. The vapor is then allowed to distribute itself throughout the chamber and into the lumen for a time period of ½ minute.

Air is then admitted into the chamber. The pressure is consequently raised to above 100 Torr within 20 seconds. The hydrogen peroxide vapors is then allowed to remain inside the chamber tube for a time period of 5 minutes. The chamber is then re-evacuated and the sterilization pulse repeated 4 times.

Example 2

The experiment in Example 1 can also be conducted wherein hydrogen peroxide vapor is introduced into a dessicated air stream which is used to perform the vapor compression. This is advantageous since the sterilant employed can be used at a higher concentration when the initial humidity is minimized.

Example 3

A bacillus steorothemophilus spore carrier is placed in the center of a more complex, 3 meter long I.V. Set. The sample is then placed inside a sterilization chamber at 0.10 Torr. A vapor compression time of one minute is applied, resulting in a 6.0 log breakdown of the spore carrier. A 15 pulse cycle using the invention is sufficient to obtain complete sterilization. The hydrogen peroxide vapor is generated from a solution of 50% hydrogen peroxide by weight.

Example 4

Provided below are results of using the current sterilization method on a 1 cm I.D.×120 cm deep passivated stainless steel deadleg. The deadlegs were placed in a 154 cubic foot chamber and maintained at 77° F. during a 4 pulse sterilization cycle. The data shows that vapor compression for 1 Torr and 2 Torr pre-injection vacuum levels penetrates deeper than an identical cycle not employing vapor compression. The vapor compression pulse went from 10 Torr to 165 Torr in 22 seconds.

| Pre-Injection Vacuum Level | Amount of Sterilant Injected per pulse | Depth of Penetration with Vapor Compression (cm) | (%) | Depth of Penetration Without Vapor Compression (cm) | (%) |
|---|---|---|---|---|---|
| 2 Torr | 56 grams | 93 | 78 | 76 | 63 |
| 1 Torr | 56 grams | 118 | 98 | 87 | 73 |

Example 5

Provided below are results of using the current sterilization method on two 1 cm I.D.×120 cm deep passivated stainless steel deadleg. The deadlegs were placed in a 154 cubic foot chamber and maintained at 77° F. during four pulse sterilization cycle. The amount of sterilant injected per pulse and the pre-injection evacuation pressure remained constant at 56 grams and 1 Torr, respectively.

| Depth of Penetration from open end (cm) | Number Positive/Number Tested for Sterility |
|---|---|
| 0 | 0/8 |
| 10 | 0/8 |
| 20 | 0/8 |
| 30 | 0/8 |
| 40 | 0/8 |
| 50 | 0/8 |
| 60 | 0/8 |
| 70 | 0/8 |
| 80 | 0/8 |
| 90 | 0/8 |
| 100 | 0/8 |
| 110 | 0/8 |
| 120 | 2/8 |

While this invention has been described in connection with preferred embodiments, it is not intended to limit the scope of the invention to particular embodiments set forth, but, to the contrary, it is intended to cover such alternatives, modifications, and equivalents as may be included within the spirit and scope of the invention as defined by the appended claims.

Example 6

The experiment in Example 1 can also be conducted wherein the sterilant vapor is generated from a solution that is a mixture of peracetic acid, acetic acid, hydrogen peroxide, and water. VigorOx Santitizer, produced by FMC, is such a solution which is 5.2% peracetic acid, 21.7% hydrogen peroxide, 10.4% acetic acid and 62.7% water.

What is claimed is:

1. A method of enhancing penetration of a low vapor pressure sterilant vapor during sterilization of an article shaped to define a narrow opening, comprising the steps of:

(a) evacuating a closed chamber containing the article to a pressure below atmospheric pressure;

(b) introducing only a sterilant vapor into the closed chamber in an amount effective to raise the pressure in the chamber to a predetermined second subatmospheric pressure;

(c) allowing the introduced amount of sterilant vapor to diffuse throughout the closed chamber and into the article for a predetermined period of time which is less than or equal to twice the half-life of the sterilant vapor in the chamber;

(d) introducing a compression gas into the closed chamber in an amount effective to raise the pressure in the chamber to a third subatmospheric pressure in a compression time period, wherein the third pressure is substantially greater than the second pressure and wherein the pressure differential between the third pressure and the second pressure is effective to drive the diffused sterilant vapor further into the article than the vapor has diffused such that the sterilant vapor substantially penetrates the article; and (e) repeating steps (a) through (d) until sterilization of the article is achieved.

2. The method of claim 1, wherein the second pressure is greater than or equal to twice the evacuation pressure.

3. The method of claim 1, wherein the third pressure is greater than six times the second pressure.

4. The method of claim 1, wherein the evacuation pressure is less than or equal to 40 Torr.

5. The method of claim 1, wherein the evacuation pressure is between about 0.1 Torr and about 10 Torr.

6. The method of claim 1, wherein the second pressure is between about 6 Torr and about 60 Torr.

7. The method of claim 1, wherein the third pressure is between about 36 Torr and 360 Torr.

8. The method of claim 1, wherein the compression time period is between about 3 seconds and about 120 seconds.

9. The method of claim 1, further comprising, between steps (d) and (e), the step of allowing the gas and the sterilant vapor to remain in the chamber for a period of time greater than or equal to the half life of the sterilant while inside the chamber.

10. The method of claim 1, wherein steps (a) through (d) are repeated between 2 and 32 times.

11. The method of claim 1, wherein the sterilant vapor is generated from an aqueous sterilant solution selected from the group consisting essentially of hydrogen peroxide, peracetic acid, acetic acid and mixtures thereof.

12. The method of claim 1, wherein the compression gas is selected from the group consisting essentially of air, dry air, helium, nitrogen and mixtures thereof.

* * * * *